US011259780B2

United States Patent
Liu et al.

(10) Patent No.: US 11,259,780 B2
(45) Date of Patent: Mar. 1, 2022

(54) ULTRASOUND MEDICAL DETECTION DEVICES AND IMAGING METHOD, IMAGING SYSTEM AND DISPLAY TERMINAL

(71) Applicant: SHENZHEN MINDRAY BIO-MEDICAL ELECTRONICS CO., LTD., Guangdong (CN)

(72) Inventors: Shuo Liu, Shenzhen (CN); Yong Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 295 days.

(21) Appl. No.: 16/541,306

(22) Filed: Aug. 15, 2019

(65) Prior Publication Data

US 2019/0374203 A1    Dec. 12, 2019

Related U.S. Application Data

(63) Continuation of application No. PCT/CN2017/073800, filed on Feb. 16, 2017.

(51) Int. Cl.
*A61B 8/00* (2006.01)
*A61B 8/06* (2006.01)
(Continued)

(52) U.S. Cl.
CPC ............. *A61B 8/463* (2013.01); *A61B 8/065* (2013.01); *A61B 8/488* (2013.01); *A61B 8/0883* (2013.01);
(Continued)

(58) Field of Classification Search
CPC ......... A61B 8/463; A61B 8/065; A61B 8/488; A61B 8/0883; A61B 8/5223; G06T 7/12;
(Continued)

(56) References Cited

U.S. PATENT DOCUMENTS 6,500,123 B1    12/2002  Holloway et al.
6,708,055 B2     3/2004  Geiser et al.
(Continued)

FOREIGN PATENT DOCUMENTS

CN    101034480 A    9/2007
CN    101449984 A    6/2009
(Continued)

OTHER PUBLICATIONS

PCT International Preliminary Report on Patentability dated Aug. 29, 2019, issued in related International Application No. PCT/CN2017/073800, with English translation (9 pages).
(Continued)

*Primary Examiner* — Bo Joseph Peng
(74) *Attorney, Agent, or Firm* — Sheppard Mullin Richter & Hampton LLP

(57) ABSTRACT

Disclosed are ultrasound medical detection devices and an imaging method, an imaging system and a display terminal. This method comprises: displaying an ultrasonic image on a first display screen, obtaining a mark point within the active area of a bicuspid valve on the ultrasonic image, automatically searching for a ventricular internal diameter reference point according to the mark point, calculating a hemodynamic parameter according to the internal diameter reference point and outputting the calculation result of the hemodynamic parameter.

25 Claims, 7 Drawing Sheets

(51) Int. Cl.
  *A61B 8/08* (2006.01)
  *G06T 7/12* (2017.01)
  *G01S 7/52* (2006.01)
  *G01S 15/89* (2006.01)
  *G06T 7/00* (2017.01)

(52) U.S. Cl.
  CPC ....... *G01S 7/52036* (2013.01); *G01S 15/8993* (2013.01); *G06T 7/0012* (2013.01); *G06T 7/12* (2017.01); *G06T 2207/10132* (2013.01); *G06T 2207/30048* (2013.01)

(58) Field of Classification Search
  CPC ......... G06T 7/0012; G06T 2207/10132; G06T 2207/30048; G06T 2207/30172; G06T 2207/30101; G06T 7/13; G01S 7/52036; G01S 15/8993; G16H 50/30
  See application file for complete search history.

(56) References Cited

U.S. PATENT DOCUMENTS

| | | | |
|---|---|---|---|
| 8,597,191 | B2 | 12/2013 | Baba et al. |
| 8,808,185 | B2 | 8/2014 | Rowlandson et al. |
| 9,153,033 | B2 | 10/2015 | Takeguchi et al. |
| 9,320,496 | B2 | 4/2016 | Datta et al. |
| 9,901,443 | B2 | 2/2018 | Morriss et al. |
| 10,674,993 | B2 | 6/2020 | Wei et al. |
| 2004/0116812 | A1 | 6/2004 | Selzer et al. |
| 2005/0075567 | A1 | 4/2005 | Skyba et al. |
| 2007/0191724 | A1 | 8/2007 | Hirsh |
| 2009/0096787 | A1* | 4/2009 | Masumoto .............. G06T 15/08 345/424 |
| 2012/0041313 | A1* | 2/2012 | Tanaka ................. A61B 8/5223 600/443 |
| 2013/0296702 | A1 | 11/2013 | Chang et al. |
| 2014/0236010 | A1 | 8/2014 | Nakano |
| 2017/0011515 | A1* | 1/2017 | Liu .......................... G06T 7/62 |

FOREIGN PATENT DOCUMENTS

| | | |
|---|---|---|
| CN | 101543405 A | 9/2009 |
| CN | 101862206 A | 10/2010 |
| CN | 102166123 A | 8/2011 |
| CN | 102883662 A | 1/2013 |
| CN | 103385735 A | 11/2013 |
| CN | 103391749 A | 11/2013 |
| CN | 103930038 A | 7/2014 |
| CN | 103974674 A | 8/2014 |
| RU | 2017124956 A | 1/2019 |

OTHER PUBLICATIONS

First Search dated Sep. 9, 2020, issued in related Chinese Application No. 201780025608.1 (2 pages).

First Office Action dated Sep. 15, 2020, issued in related Chinese Application No. 201780025608.1, with English machine translation (7 pages).

Supplemental Search dated Apr. 1, 2021, issued in related Chinese Application No. 201780025608.1 (1 page).

Xiang-hong Luo et al., "Evaluation of respiratory influence on interventricular septum by radius of curvature", China J. Med. Imaging Technol., vol. 25, No. 1, 2009, pp. 76-78, with English abstract.

Xingchen97, "Cardiac ultrasound measurement specification and development", Baidu Library, Apr. 19, 2015.

PCT International Search Report and the Written Opinion dated Nov. 27, 2017, issued in related International Application No. PCT/CN2017/073800 (9 pages).

* cited by examiner

ULTRASOUND MEDICAL DETECTION DEVICES AND IMAGING METHOD, IMAGING SYSTEM AND DISPLAY TERMINAL

CROSS-REFERENCE TO RELATED APPLICATIONS

This application is a continuation of PCT Application No. PCT/CN2017/073800, filed on Feb. 16, 2017 and entitled "ULTRASOUND MEDICAL DETECTION DEVICES AND IMAGING METHOD, IMAGING SYSTEM AND DISPLAY TERMINAL", which is incorporated herein by reference in its entirety.

TECHNICAL FIELD

The present disclosure relates to an ultrasound medical detection device and imaging method, imaging system and display terminal.

BACKGROUND

Hemodynamics is a science of studying a heart generating power to push the blood to flow in the vascular system to infuse tissue. The quality of blood perfusion is directly related to the function of vital organs of life. The dysfunction of vital organs is directly or indirectly closely related to hemodynamic changes. Therefore, a hemodynamic monitoring will be helpful in understanding the development of the disease and guiding clinical treatment. So far, the hemodynamic monitoring method has been developed from invasive monitoring to non-invasive monitoring. In the invasive monitoring method, a catheter or probe is inserted into the heart chamber or the vascular cavity through the body surface to directly measure the cardiovascular function parameters, specifically including an arterial blood pressure, a central venous pressure, a Swan-Ganz catheter and a PiCCO (pulse index continuous cardiac output monitoring). In the non-invasive monitoring method, the methods which have no mechanical damage to the body are used to obtain various cardiovascular function parameters.

Echocardiography is a preferred non-invasive technique for examining the anatomical structure and functional status of the heart and the large blood vessels utilizing the special physical properties of ultrasound.

A probe transmits an ultrasound beam which passes through various layers of the heart. The reflected echo is received in the gap of the transmission of the ultrasound waves by the probe, and converted into electric energy by the positive piezoelectric effect, which then is detected and amplified, and displayed as a strong or weak spot on a fluorescent screen. The ultrasound pulses constantly penetrate the tissue and produce echoes. The sound waves reflected at different times are displayed on the fluorescent screen in a series of longitudinally arranged light spots according to the order of the reflective interfaces. In 1954, ultrasound was first used to diagnose heart disease. There are three types of echocardiography commonly used in clinical practice: M-type, two-dimensional and Doppler echocardiography. Currently, the echocardiography has become a common method for estimating cardiac function in clinic.

It is therefore desired to provide a way for easily obtain cardiac functions using echocardiography.

SUMMARY

In one embodiment, an ultrasound medical detection device is provided, which may include:
a probe;
a transmitting circuit and a receiving circuit which excite the probe to transmit an ultrasound beam to an object containing a heart tissue and receive an echo of the ultrasound beam to obtain an ultrasound echo signal;
an image processor which obtains an ultrasound image according to the ultrasound echo signal;
a first display;
a first memory which stores a computer program to be executed by the processor; and
a first processor which, when executing the program, performs following steps:
displaying the ultrasound image on the first display;
obtaining a mark point located in a mitral valve active area on the ultrasound image;
automatically searching for a ventricular inner diameter reference point according to the mark point;
calculating a hemodynamic parameter according to the ventricular inner diameter reference point; and
outputting a calculation result of the hemodynamic parameter.

In one embodiment, an ultrasound imaging method is provided, which may include:
displaying an ultrasound image on a display, wherein the ultrasound image is obtained according to an ultrasound echo signal, and wherein the ultrasound echo signal is obtained by receiving an echo of an ultrasound beam which is transmitted to an object containing a heart tissue by exciting a probe;
obtaining a mark point in a mitral valve active area in the ultrasound image;
automatically searching for a ventricular inner diameter reference point according to the mark point; and
calculating a hemodynamic parameter according to the inner diameter reference point.

In one embodiment, an ultrasound imaging system is provided, which may include an ultrasound medical detection device and an ultrasound display terminal, where
the ultrasound medical detection device comprises:
a probe;
a transmitting circuit and a receiving circuit which excite the probe to transmit an ultrasound beam to an object containing a heart tissue and receive an echo of the ultrasound beam to obtain an ultrasound echo signal;
an image processor which obtains an ultrasound image according to the ultrasound echo signal; and
a first communication device which is connected with the image processor and used to transmit the ultrasound image to the ultrasound display terminal; and
the ultrasound display terminal comprises:
a second display,
a second communication device which receives the ultrasound image transmitted from the first communication device;
a second memory which stores a computer program to be executed by a processor; and
a second processor which, when executing the program, performs following steps:
displaying the ultrasound image on the second display;
obtaining a mark point located in a mitral valve active area on the ultrasound image;
automatically searching for a ventricular inner diameter reference point according to the mark point;
calculating a hemodynamic parameter according to the ventricular inner diameter reference point; and
outputting a calculation result of the hemodynamic parameter.

In one embodiment, an ultrasound display terminal is provided, which may include:

a second display;

a second communication device which receives an ultrasound image transmitted from an ultrasound medical detection device;

a second memory which stores a computer program to be executed by a processor; and a second processor which, when executing the program, performs following steps:

displaying the ultrasound image on the second display;

obtaining a mark point located in a mitral valve active area on the ultrasound image;

automatically searching for a ventricular inner diameter reference point according to the mark point;

calculating a hemodynamic parameter according to the ventricular inner diameter reference point; and outputting a calculation result of the hemodynamic parameter.

In one embodiment, an ultrasound medical detection device is provided. The ultrasound medical detection device may include a probe, a transmitting circuit, a receiving circuit, a first display, a first memory and a processor. The transmitting circuit may excite the probe to transmit an ultrasound beam to an object containing a heart tissue, the receiving circuit may receive an echo of the ultrasound beam to obtain an ultrasound echo signal, and the first memory may store a computer program to be executed by a processor.

The processor may execute the program stored in the first memory. When executing the program, the processor may obtain an ultrasound image according to the ultrasound echo signal, display the ultrasound image on the first display, obtain a mark point located in a mitral valve active area on the ultrasound image, automatically search for a ventricular inner diameter reference point according to the mark point, calculate a hemodynamic parameter according to the ventricular inner diameter reference point, and output the calculated hemodynamic parameter.

In one embodiment, the ultrasound image may be a left ventricular long axis section image.

In one embodiment, when executing the program, the processor may automatically obtains a M line according to the ventricular inner diameter reference point, and automatically calculates the hemodynamic parameter according to the M line.

In one embodiment, when executing the program, the processor may automatically search for a position of a mitral valve tip in an area where the mark point is located, automatically search for a ventricular posterior wall skeleton line, search for a proximity point which is closest to the position of the mitral valve tip on the ventricular posterior wall skeleton line, and move a position of the proximity point with reference to a slope of the proximity point on the ventricular posterior wall skeleton line to obtain the ventricular inner diameter reference point.

In one embodiment, the ventricular inner diameter reference point may deviate from a proximity point which is a position on a ventricular posterior wall skeleton line closest to a position of a mitral valve tip, and the ventricular inner diameter reference point deviates from the proximity point in a direction away from the position of the mitral valve tip.

In one embodiment, when executing the program, the processor may obtain the mark point located in the mitral valve active area in the ultrasound image by one of:

obtaining the mark point acquired by an user on the ultrasound image through a human-machine interaction device; and obtaining an area range containing the mitral valve active area determined by an user on the ultrasound image through a human-machine interaction device and determining a position of any point in the area range as a position corresponding to the mark point.

In one embodiment, when executing the program, the processor may search for a foot of perpendicular from the ventricular inner diameter reference point to the ventricular posterior wall skeleton line which is closest to the ventricular inner diameter reference point, and connect the ventricular inner diameter reference point and the foot of perpendicular to obtain the M line.

In one embodiment, the position of the mitral valve tip may be obtained by automatically searching for a connected area which is closest to the mark point, and the ventricular posterior wall skeleton line may be obtained by searching for a largest connected area and extracting a center line of the largest connected area along a length direction thereof.

In one embodiment, when executing the program, the processor may further output an alarm prompt to prompt that an output result is invalid.

In one embodiment, when executing the program, the processor may automatically search for connected areas closest to the mark point in consecutive multiples frames of images, and output the alarm prompt when it is determined that the connected areas respectively obtained in the consecutive multiple frames of images do not overlap; or automatically search for a maximum connected area and a connected area closest to the mark point in the ultrasound image, and output the alarm prompt when it is determined that the maximum connected area and the obtained connected area closest to the one marked point do not satisfy an anatomical structure characteristic or the maximum connected areas obtained in adjacent two frames of ultrasound images do not overlap.

In one embodiment, when executing the program, the processor may plots an M image along a time axis according to grayscale of each point on the M line, extracts an upper edge and a lower edge of a ventricle in the M image to obtain a ventricular inner diameter length, and obtain a maximum and/or a minimum of the ventricular inner diameter length based on the ultrasound images in an end-diastolic and/or an end-systolic phase to calculate the hemodynamic parameter, thereby achieving automatically calculating the hemodynamic parameter according to the M line.

In one embodiment, an ultrasound imaging method is provided, which may include:

displaying an ultrasound image on a display, wherein the ultrasound image is obtained according to an ultrasound echo signal, and wherein the ultrasound echo signal is obtained by receiving an echo of an ultrasound beam which is transmitted to an object containing a heart tissue by exciting a probe;

obtaining a mark point in a mitral valve active area in the ultrasound image;

automatically searching for a ventricular inner diameter reference point according to the mark point; and calculating a hemodynamic parameter according to the inner diameter reference point.

In one embodiment, calculating the hemodynamic parameter according to the inner diameter reference point may include automatically obtaining an M line according to the ventricular inner diameter reference point, and automatically calculating the hemodynamic parameter according to the M line.

In one embodiment, automatically searching for the ventricular inner diameter reference point according to the mark point may include:

automatically searching for a position of a mitral valve tip in an area where the mark point is located;

automatically searching for a ventricular posterior wall skeleton line;

searching for a proximity point on the ventricular posterior wall skeleton line which is closest to the position of the mitral valve tip; and moving a position of the proximity point with reference to a slope of the proximity point on the ventricular posterior wall skeleton line to obtain the ventricular inner diameter reference point.

In one embodiment, the ventricular inner diameter reference point may deviate from a proximity point which is a position on a ventricular posterior wall skeleton line closest to a position of a mitral valve tip, and the ventricular inner diameter reference point may deviate from the proximity point in a direction away from the position of the mitral valve tip.

In one embodiment, obtaining the mark point in the mitral valve active area in the ultrasound image may include obtaining the mark point acquired by an user on the ultrasound image through a human-machine interaction device, or, obtaining an area range containing the mitral valve active area determined by an user on the ultrasound image through a human-machine interaction device and determining a position of any point in the area range as a position corresponding to the mark point.

In one embodiment, automatically obtaining the M line according to the ventricular inner diameter reference point may include searching for a foot of perpendicular from the ventricular inner diameter reference point to the ventricular posterior wall skeleton line which is closest to the ventricular inner diameter reference point and connecting the ventricular inner diameter reference point and the foot of perpendicular to obtain the M line.

In one embodiment, automatically searching for the position of the mitral valve tip in the area where the mark point is located may include automatically searching for a connected area which is closest to the mark point to obtain the position of the mitral valve tip, and automatically searching for the ventricular posterior wall skeleton line may include searching for a largest connected area and extracting a center line of the largest connected area along a length direction thereof to obtain the ventricular posterior wall skeleton line.

In one embodiment, the method may further include outputting an alarm prompt to prompt that an output result is invalid.

In one embodiment, outputting the alarm prompt to prompt that an output result is invalid may include automatically searching for connected areas closest to the mark point in consecutive multiples frames of images and outputting the alarm prompt when it is determined that the connected areas respectively obtained in the consecutive multiple frames of images do not overlap.

In one embodiment, outputting the alarm prompt to prompt that an output result is invalid may include automatically searching for a maximum connected area and a connected area closest to the mark point in the ultrasound image and outputting the alarm prompt when it is determined that the maximum connected area and the obtained connected area closest to the one marked point do not satisfy an anatomical structure characteristic or the maximum connected areas obtained in adjacent two frames of ultrasound images do not overlap.

In one embodiment, automatically calculating the hemodynamic parameter according to the M line may include:

plotting an M image along a time axis according to grayscale of each point on the M line;

extracting an upper edge and a lower edge of a ventricle in the M image to obtain a ventricular inner diameter length; and obtaining a maximum and/or a minimum of the ventricular inner diameter length based on the ultrasound images in an end-diastolic and/or an end-systolic phase to calculate the hemodynamic parameter.

In one embodiment, an ultrasound imaging system is provided. The ultrasound imaging system may include an ultrasound medical detection device and an ultrasound display terminal.

The ultrasound medical detection device may include a probe, a transmitting circuit, a receiving circuit, an image processor and a first communication device. The transmitting circuit may excite the probe to transmit an ultrasound beam to an object containing a heart tissue. The receiving circuit may receive an echo of the ultrasound beam to obtain an ultrasound echo signal. The image processor may obtain an ultrasound image according to the ultrasound echo signal. The first communication device may be connected with the image processor and used to transmit the ultrasound image to the ultrasound display terminal.

The ultrasound display terminal may include a second display, a second communication device, a second memory and a second processor. The second communication device may receive the ultrasound image transmitted from the first communication device. The second memory may store a computer program to be executed by a processor. The second processor may, when executing the program, display the ultrasound image on the second display, obtain a mark point located in a mitral valve active area on the ultrasound image, automatically search for a ventricular inner diameter reference point according to the mark point, calculate a hemodynamic parameter according to the ventricular inner diameter reference point, and output a calculation result of the hemodynamic parameter.

In one embodiment, when executing the program, the second processor may automatically obtain an M line according to the ventricular inner diameter reference point and automatically calculate the hemodynamic parameter according to the M line.

In one embodiment, when executing the program, the second processor may obtain the mark point acquired by an user on the ultrasound image through a human-machine interaction device. Alternatively, the second processor may obtain an area range containing the mitral valve active area determined by an user on the ultrasound image through a human-machine interaction device and determines a position of any point in the area range as a position corresponding to the mark point.

In one embodiment, when executing the program, the second processor may search for a foot of perpendicular from the ventricular inner diameter reference point to the ventricular posterior wall skeleton line which is closest to the ventricular inner diameter reference point and connect the ventricular inner diameter reference point and the foot of perpendicular to obtain the M line.

In one embodiment, when executing the program, the second processor may further output an alarm prompt to prompt that an output result is invalid.

In one embodiment, an ultrasound display terminal is provided, which may include a second display, a second communication device, a second memory and s second processor. The second communication device may receive an ultrasound image transmitted from an ultrasound medical detection device. The second memory may store a computer program to be executed by a processor. The second processor may, when executing the program, display the ultrasound image on the second display, obtain a mark point located in a mitral valve active area on the ultrasound image, automatically search for a ventricular inner diameter reference point according to the mark point, calculate a hemodynamic parameter according to the ventricular inner diameter reference point, and output a calculation result of the hemodynamic parameter.

In one embodiment, when executing the program, the second processor may:

automatically search for a position of a mitral valve tip in an area where the mark point is located;

automatically search for a ventricular posterior wall skeleton line;

search for a proximity point on the ventricular posterior wall skeleton line which is closest to the position of the mitral valve tip; and move a position of the proximity point with reference to a slope of the proximity point on the ventricular posterior wall skeleton line to obtain the ventricular inner diameter reference point.

In one embodiment, when executing the program, the second processor may obtain the position of the mitral valve tip by automatically searching for a connected area which is closest to the mark point.

In one embodiment, when executing the program, the second processor may obtain the ventricular posterior wall skeleton line by searching for a largest connected area and extracting a center line of the largest connected area along a length direction thereof.

In one embodiment, when executing the program, the second processor may further output an alarm prompt to prompt that an output result is invalid.

In one embodiment, when executing the program, the second processor may output the alarm prompt to prompt that the output result is invalid by automatically searching for connected areas closest to the mark point in consecutive multiples frames of images and outputting the alarm prompt when it is determined that the connected areas respectively obtained in the consecutive multiple frames of images do not overlap.

Alternatively, when executing the program, the second processor may output the alarm prompt to prompt that the output result is invalid by automatically searching for a maximum connected area and a connected area closest to the mark point in the ultrasound image and outputting the alarm prompt when it is determined that the maximum connected area and the obtained connected area closest to the one marked point do not satisfy an anatomical structure characteristic or the maximum connected areas obtained in adjacent two frames of ultrasound images do not overlap.

In one embodiment, when executing the program, the second processor may plot an M image along a time axis according to grayscale of each point on the M line, extracts an upper edge and a lower edge of a ventricle in the M image to obtain a ventricular inner diameter length, and obtain a maximum and/or a minimum of the ventricular inner diameter length based on the ultrasound images in an end-diastolic and/or an end-systolic phase to calculate the hemodynamic parameter.

In one embodiment, a computer readable storage medium is provided, which may store a plurality of instructions. The plurality of instructions may, when executed by a processor, cause the processor to:

display an ultrasound image on a display;

obtain a mark point in a mitral valve active area in the ultrasound image;

automatically search for a ventricular inner diameter reference point according to the mark point; and calculate a hemodynamic parameter according to the inner diameter reference point.

BRIEF DESCRIPTION OF THE DRAWINGS

FIG. 6(A) shows the grayscale of all points on the M line in FIG. 5, and the abscissa is the point order of the M line in FIG. 5 while the ordinate is the gray level of the point on the M line; and in FIG. 6(B), the abscissa is the point order of the M line in FIG. 5 and the ordinate is the corresponding absolute value of the gradient of grayscale in FIG. 6(A).

DETAILED DESCRIPTION

The present disclosure will be further described in detail below by specific embodiments with reference to the drawings. Similar elements in different embodiments employ associated similar reference numbers. In the following embodiments, many of the details are described in order to provide a better understanding of the application. However, those skilled in the art can easily understand that some of the features may be omitted in different situations, or may be replaced by other components, materials, or methods. In some cases, some operations related to the present application have not been shown or described in the specification, in order to avoid that the core portion of the present application is overwhelmed by excessive description. For those skilled in the art, the detailed description of these operations will not be necessary because they can fully understand these operations according to the description in the specification and the general technical knowledge in the art.

In addition, the features, operations, or characteristics described in the specification may be combined in any suitable manner to form various embodiments. Furthermore, the steps or actions in the method description can also be changed or adjusted in execution sequence in a manner that can be apparent to those skilled in the art. Therefore, the various sequences in the specification and the drawings are only for the purpose of describing clearly a particular embodiment, and are not intended to be necessary sequence, unless otherwise stated that a certain sequence must be followed.

The serial numbers themselves of the components herein, such as "first", "second", etc., are only used to distinguish the described objects, but do not have any order or technical meaning. As used herein, "connection" or "coupling", unless otherwise specified, includes both direct and indirect connection (coupling).

Figure 1:
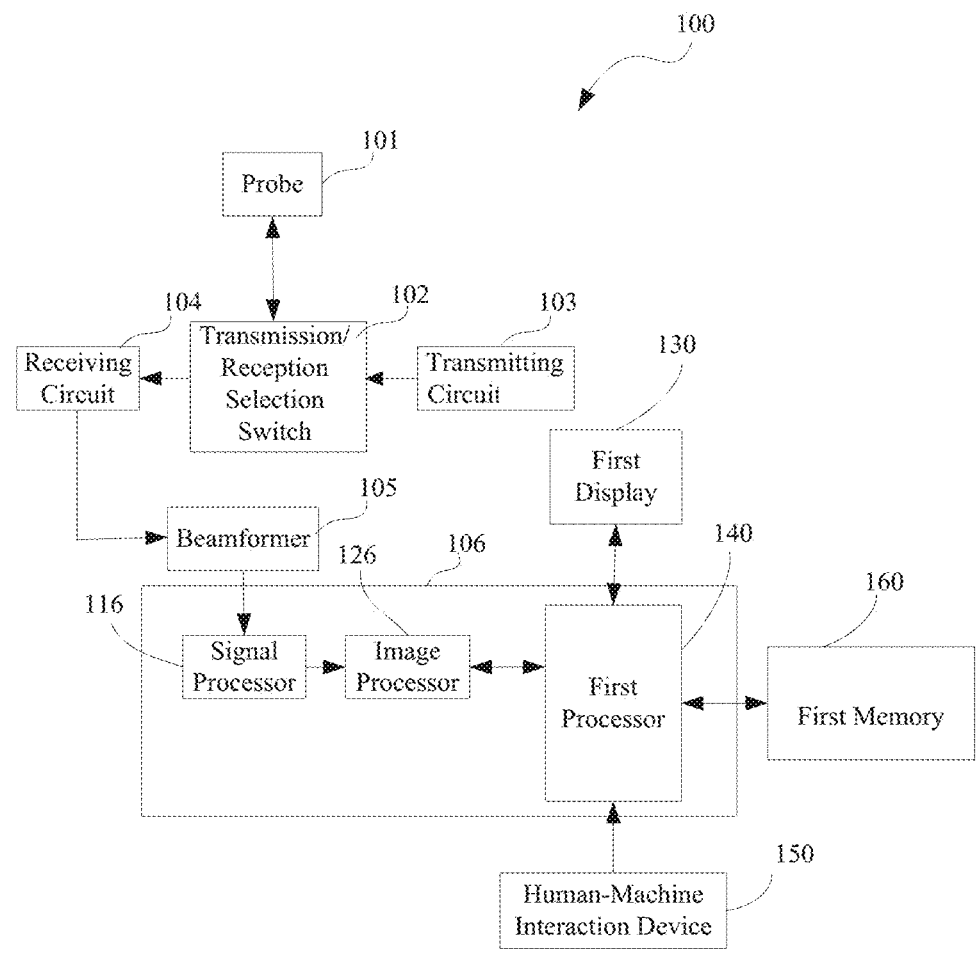
FIG. 1 is a schematic diagram of the system architecture of an ultrasound medical detection device in one embodiment.

FIG. 1 is a schematic view showing the structure of an ultrasound medical detection device 100 in one embodiment, the specific structure of which is as follows. The ultrasound medical detection device 100 shown in FIG. 1 may mainly include a probe 101, a transmitting circuit 103, a transmission/reception selection switch 102, a receiving circuit 104, a beamformer 105, a signal processor 116, and an image processor 126. In the ultrasound imaging process, the transmitting circuit 103 may transmit a delay-focused transmission pulse having a certain amplitude and polarity to the probe 101 through the transmission/reception selection switch 102. The probe 101 may be excited by the transmission pulse to transmit an ultrasound wave (which may be any one of a plane wave, a focused wave and a divergent wave) to an object containing cardiac tissue (for example, heart tissue and blood vessels thereof in a human body or an animal body, etc., not shown), and receive an ultrasound echo with information of the object reflected from the target area after a certain delay and reconvert the ultrasound echo into an electrical signal. The receiving circuit 104 may receive the electrical signals generated by the probe 101 to obtain ultrasound echo signals, and send the ultrasound echo signals to the beamformer 105. The beamformer 105 may perform processing such as focus-delay, weighting and channel summation, etc. on the ultrasound echo signals, and then send the ultrasound echo signals to the signal processor 116 where related signal processing will be performed thereon. The ultrasound echo signals processed by the signal processor 116 may be sent to the image processor 126. The image processor 126 may perform different processing on the signals according to different imaging modes desired by the user to obtain ultrasound image data of different modes, and then form ultrasound images of different modes by processing of logarithmic compression, dynamic range adjustment, digital scan conversion, and the like, such as B image, C image, D image, etc., or other types of two-dimensional or three-dimensional ultrasound images. The transmitting circuit and the receiving circuit may excite the probe to transmit an ultrasound beam to the object according to set ultrasound imaging parameters and receive an echo of the ultrasound beam to obtain ultrasound echo signals, thereby obtaining desired ultrasound image data for displaying so as to present the internal structure of the heart. The ultrasound imaging parameters mentioned herein may refer to all parameters that can be selected by the user during the imaging process of the ultrasound tissue images, such as TGC (Time Gain Compensate), acoustic frequency, pulse recurrence frequency (PRF), ultrasound type, and dynamic range, etc.

In one embodiment, the signal processor 116 and the image processor 126 of FIG. 1 may be integrated on one main board 106, or one or more of the modules may be integrated in one processor/controller chip.

The ultrasound medical detection device 100 may further include a first display 130, a first processor 140, a first memory 160 and a human-machine interaction device 150. The first processor may be configured to output the obtained ultrasound image to the first display 130 for displaying. The first processor 140 may call the computer program instructions stored in the first memory 160 to display the ultrasound image on the first display 130, and acquire a control instruction input by the user on the displayed ultrasound image through the human-machine interaction device. The human-machine interaction device herein may include one of a keyboard, a scroll wheel, a mouse and a touch screen, etc., and the first display 130 may also be a normal display or a touch screen. In the case that the first display 130 is a touch screen, the human-machine interaction device 150 may also be a touch screen. Accordingly, during acquiring the control instruction input by the user on the displayed ultrasound image through the human-machine interaction device, the first processor 140 may call the computer program instructions stored in the first memory 160 to know the contact of the input object on the touch screen, thereby determining the control instruction input by the user on the displayed ultrasound image.

Regarding the first processor 140 calling the computer program instructions stored in the first memory 160 to know the contact of the input object (e.g. the index finger, the thumb, the stylus, the touch screen dedicated pen, etc.) on the touch screen, an ultrasound image may be displayed on the touch screen first, and then the first processor 140 may call a gesture detection module stored in the memory 160 to detect a contact operation of the user on a graphical user interface through the input object, thereby obtaining the control instruction. In various embodiments, a touch screen having a graphical user interface (GUI), one or more processors, a memory, and one or more modules, programs or instruction sets stored in the memory for performing various functions may be provided, which together implement a graphical user interface (GUI)-based manipulation input detection to obtain the relevant control instructions. In various embodiments, the functions may include the parameter adjustment, information input, marker position input, etc. to the ultrasound image of the object (e.g. the tissue of the patient) for obtaining medical detection data, image browsing, construction, retrieval and maintenance of pathology database, construction, display and management of patient file, construction, display and management of patient directory, etc. The modules, programs, or instructions for executing these functions may be included in a computer program product configured for execution by one or more processors. In some of the embodiments of the present disclosure, the user may interact with the graphical user interface mainly through gesture input on the touch screen. The gesture input herein may include any type of user gesture input that the device is enabled to detect by directly touching or closing the touch screen. For example, the gesture input may be an action of selecting one position, multiple positions and/or multiple continuous positions on the touch screen of the user through a finger of a right or left hand (e.g., an index finger, a thumb, etc.) or through an input object (e.g., a stylus, a touch screen dedicated pen), including operational actions such as contact, touch release, touch tap, long contact, rotational deployment, and the like. Here, the long contact corresponds to a gesture input of moving a finger, a thumb, a stylus in a predetermined direction or a variable direction while the finger, the thumb, the stylus, or the like is kept in continuous contact with the touch screen, such as the gesture operation of touch dragging, flicking, wiping, sliding, sweeping, and the like. It can be seen that the gesture input may be achieved by the contact of the input object with the touch screen, and the contact with the touch screen may include direct contact with or close, without direct contact, to the touch screen of the finger, the thumb, or the stylus, etc. The gesture input that is close to the touch screen without direct contact may refer to a gesture operation action in a spatial position proximate to the touch screen. The graphical user interface above may refer to an overall design of human-computer interaction, operation logic and interface aesthetics of the software, which may include one or more soft keyboards and multiple graphic control objects. A soft keyboard may include a number of icons (or soft keys). This allows the user to select one or more icons in the soft keyboard and thus select one or more corresponding symbols for input. The gesture detection module can detect a gesture input by which the input object interacts with the touch screen. The gesture detection module may include various program modules used for performing various operations related to the gesture input detection, such as the various steps of determining whether a contact has occurred, determining whether the gesture input is continuously input, determining whether the gesture input corresponds to a predetermined gesture, determining an operation position corresponding to the gesture input, determining whether the operation position corresponding to the gesture input is moved to an edge position of a corresponding display area, determining whether the gesture input has been interrupted (e.g., whether the contact has been stopped), determining the movement of the gesture input and tracking the movement trajectory of the gesture input. Determining the movement of the gesture input may include determining a rate (amplitude) of the movement, a velocity (amplitude and direction) of the movement, and/or an acceleration (a change in the amplitude and/or the direction), the trajectory of the movement, and the like, of the operation position corresponding to the gesture input. These operations can be applied to a single operational position (e.g., a gesture input implemented by one finger), or multiple simultaneous operational positions (e.g., "multi-touch", i.e., gesture input implemented by multiple fingers). In one embodiment, the gesture detection module may be used to detect the movement of one or more input objects on a touch screen surface or at a spatial location proximate to the touch screen. The gesture detection module may be stored in the memory, and may be called by one or more processors to implement the monitoring of the gesture input above to obtain the operation input instruction of the user.

Figure 3:
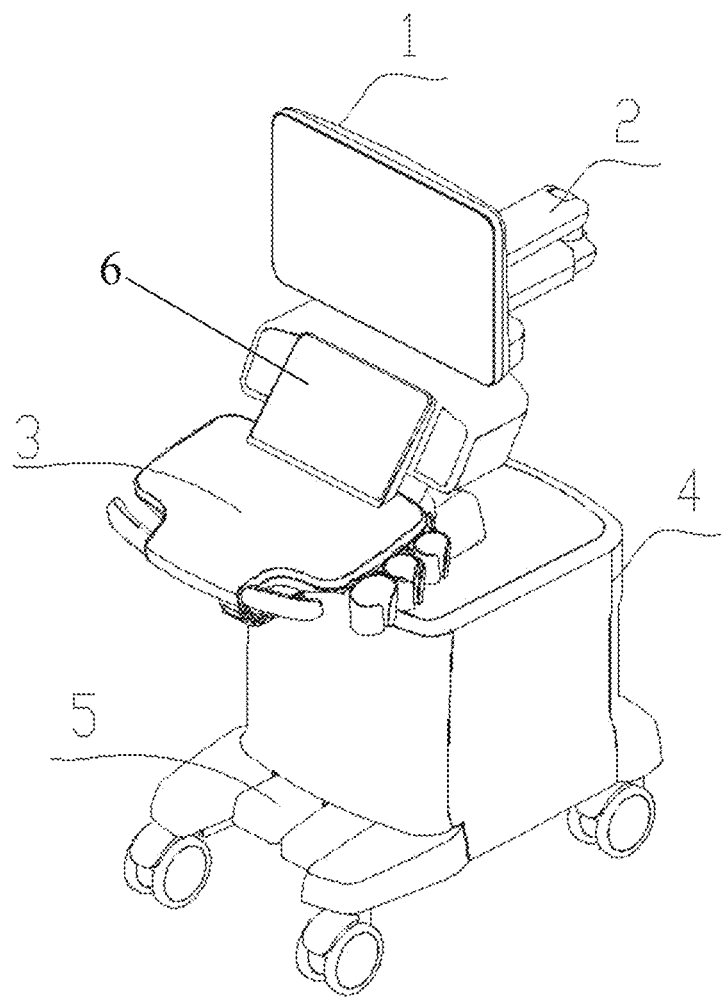
FIG. 3 is a schematic diagram of the system architecture of an ultrasound detection system in one embodiment.

In the embodiment shown in FIG. 1, the first processor 140 and the first memory 160 may be disposed on the main board 106, or may be disposed independently of the main board 106. Alternatively, the first processor 140 and the first memory 160 may be integrated with the touch screen to form an independent display controller which can not only achieve the display of the ultrasound image but also achieve obtaining the control instruction input by the user based on the ultrasound image. The control instruction obtained by the display controller may be output to the ultrasound medical detecting device 100 for controlling the scanning of the probe or the formation of the ultrasound image. In one embodiment, as shown in FIG. 3, an ultrasound medical detection device may include a display 1, a control key operating area 3, a display support arm 2, a main body 4, and a foot control 5. The display 1 may be the same as the first display described above, and the main body 4 may include the main board 106 described above or further include the first processor 140 and the first memory 160. In FIG. 3, a portable IPAD terminal controller 6 may further be provided, which may be the same as the display controller mentioned above and implement the same functions as the first display and human-machine interaction devices described above.

Figure 2:
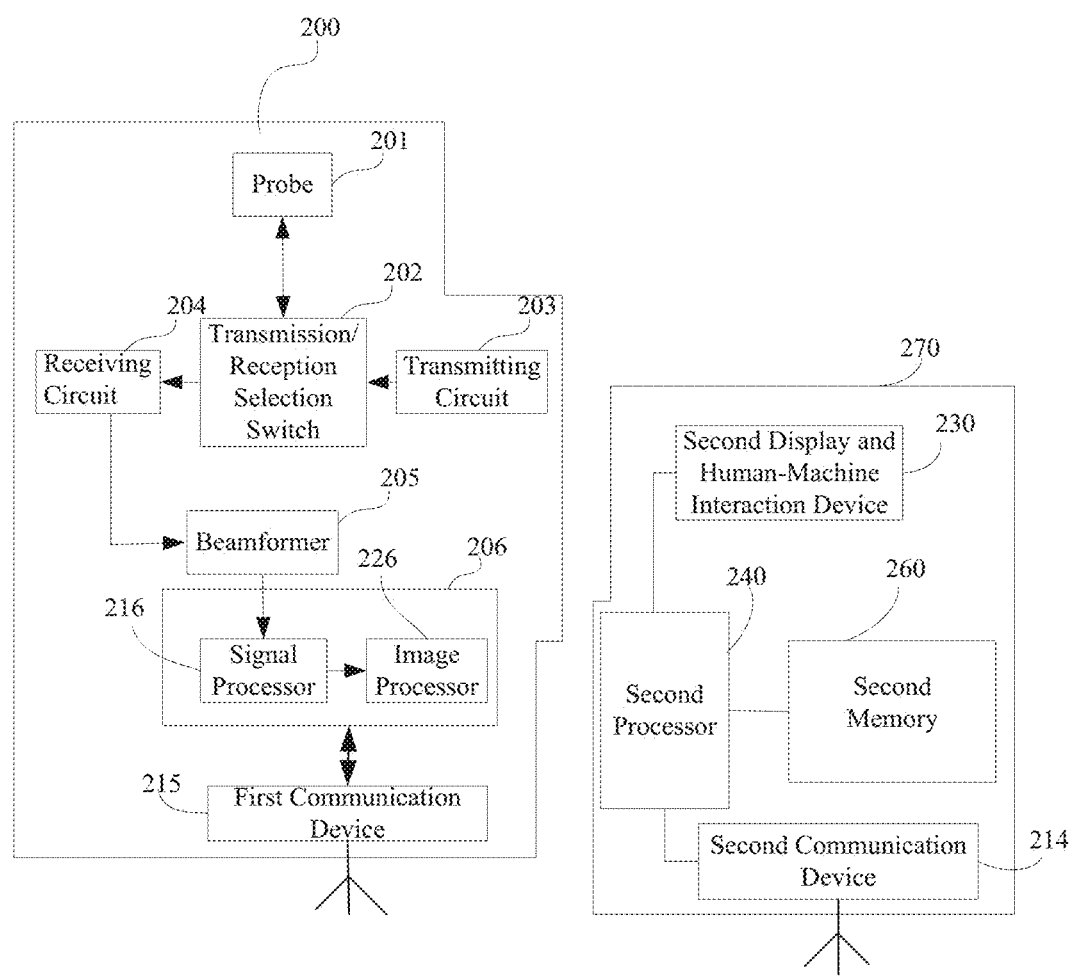
FIG. 2 is a schematic diagram showing the architecture of an ultrasound imaging system in one embodiment.

FIG. 2 is a schematic view of the structure of another embodiment. As shown in FIG. 2, the ultrasound medical detection device 200 may include a probe 201, a transmitting circuit 203, a transmission/reception selection switch 202, a receiving circuit 204, a beamformer 205, a signal processor 216 and an image processor 226. In this embodiment, the functions and implementations thereof implemented by the probe 201, the transmitting circuit 203, the transmission/reception selection switch 202, the receiving circuit 204, the beamformer 205, the signal processor 216 and the image processor 226 may be the same as those implemented by the probe 101, the transmitting circuit 103, the transmission/reception selection switch 102, the receiving circuit 104, the beamformer 105, the signal processor 116 and the image processor 126 in the embodiments shown in FIG. 1, and will not be described again here. In one embodiment, the signal processor 216 and the image processor 226 of FIG. 2 may be integrated in one main board 206. Alternatively, one or more of the modules thereof may be integrated in one processor/controller chip. The difference from the embodiment shown in FIG. 1 is that the ultrasound medical detection device 200 may further include a first communication device 215 connected to the image processor 226 for transmitting the ultrasound image data obtained by the image processor 226 to an ultrasound display terminal 270 and/or receiving a control signal input by the ultrasound display terminal 270. For example, the control signal may be used to set the ultrasound imaging parameters used in the ultrasound imaging process. Setting the ultrasound imaging parameters may include updating the ultrasound imaging parameters, adjusting the ultrasound imaging parameters, or initializing the ultrasound imaging parameters, etc. The ultrasound display terminal 270 in this embodiment may include a second display and human-machine interaction device 230, a second processor 240, a second memory 260, and a second communication device 214. The second memory 260 may store the computer program to be executed in the second processor 240, such as the aforementioned gesture detection module. The second display and human-machine interaction device 230 may be a touch screen, similar to the touch screen mentioned in the foregoing embodiment of FIG. 1. In this embodiment, the second display and human-machine interaction device 230 may have the same functions as the first display 130 and the human-machine interaction device 150 in FIG. 1, and reference may be made to the description above. The second communication device 214 may receive the ultrasound image (or ultrasound image data) transmitted from the first communication device 215, and/or transmit a control signal (such as a control signal containing ultrasound imaging parameter setting information) or various data such as calculation results related to the ultrasound image to the first communication device 215. In addition, the second communication device 214 may also transmit the ultrasound image data and/or the control signal to other external output devices (such as other display controllers or smart terminal devices). The ultrasound display terminal 270 may include the display controller mentioned in FIG. 1 or the IPAD terminal controller 6 in FIG. 3, and may also include various smart terminal devices, such as intelligent computer devices such as an IPAD, a mobile phone, a workstation, a network server, and the like. For example, the ultrasound display terminal 270 in this embodiment may also be the IPAD terminal controller 6 in FIG. 3. The communication between the first communication device 215 and the second communication device 214 may be implemented by a wireless data transmission protocol such as a wifi protocol, a Bluetooth transmission protocol, a mobile communication network protocol, or the like. The ultrasound medical detection device 200 and the ultrasound display terminal 270 may form an ultrasound imaging system.

In the embodiment shown in FIG. 3, an ultrasound imaging system or an ultrasound medical detection device 100 is provided which may integrate two displays, i.e. a display 1 and an IPAD terminal controller 6. The IPAD terminal controller 6 may be used to generate a graphical user interface to obtain user's instructions regarding ultrasound imaging parameter adjustment, or perform editing operations on an ultrasound image (including any input operation based on the ultrasound image), or display the ultrasound image and/or the remark information obtained after the editing operation above (the remark information may include probe position icon, sampling gate position, M line, etc.). The IPAD terminal controller 6 may also include a second display and human-machine interaction device 230, such as a touch screen. Regarding the IPAD terminal controller 6 equivalent to the ultrasound display terminal 270, the same function may also be implemented by intelligent mobile terminal such as a smart phone, etc. The M line herein may refer to the sampling line in the ultrasound M-type sampling mode.

Based on the structural view of the ultrasound medical detection device (100, 200) and the ultrasound display terminal 270 shown in FIG. 1, FIG. 2 or FIG. 3 above, related ultrasound imaging methods will be described in detail with reference to the hardware environment provided in FIG. 1, FIG. 2 or FIG. 3. Reference may be specifically made to the flowchart shown in FIG. 4.

Figure 4:
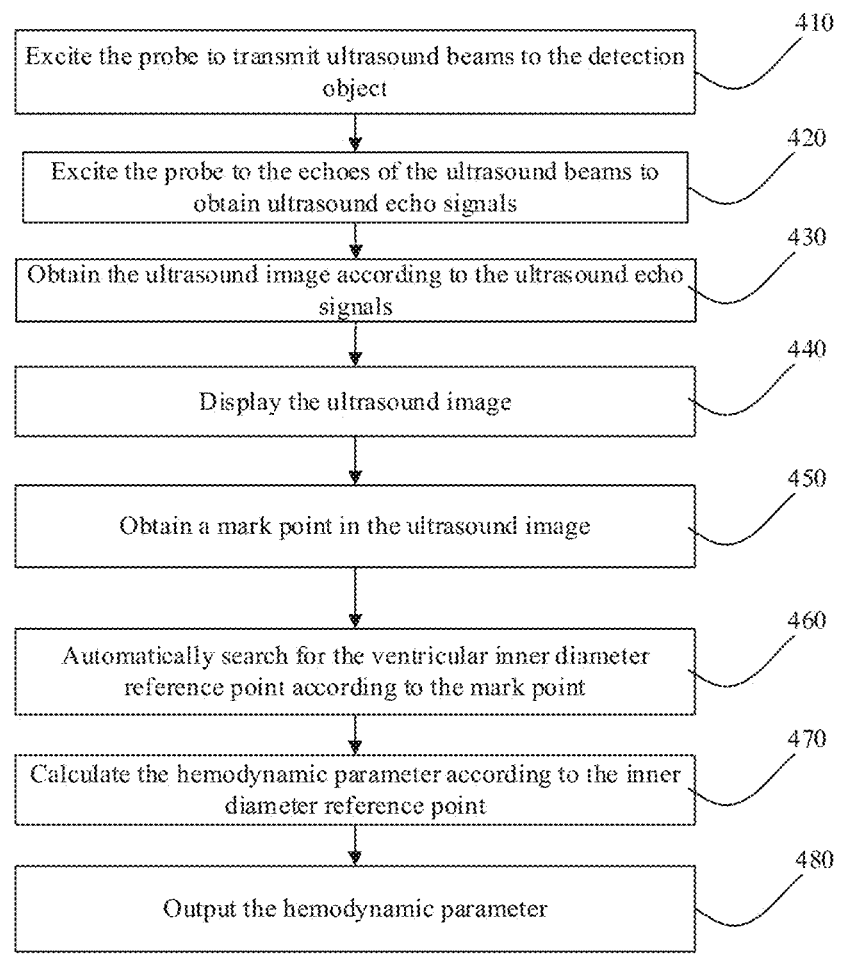
FIG. 4 is a schematic flow chart of an ultrasound imaging control method in the embodiment shown in FIG. 1 or FIG. 2.

In steps 410 and 420 of FIG. 4, the transmitting circuit and the receiving circuit (103 and 104, or 203 and 204 in FIG. 2) may excite the probe (101, or 201 in FIG. 2) according to the set ultrasound imaging parameters to transmit an ultrasound beam to the object containing the heart tissue and receive echoes of the ultrasound beam to obtain the ultrasound echo signals. In one embodiment, the ultrasound imaging parameters in the present embodiment may include position information of the sampling gate, the position of the M line, and the like, which may be obtained, for example, according to a mark input by the user on the ultrasound image.

In step 430 of FIG. 4, the image processor (126, or 226 in FIG. 2) may obtain an ultrasound image, such as an M-mode echocardiogram, from the ultrasound echo signals. The ultrasound image herein may be an image containing the heart tissue structure. In the ultrasound medical detection device of FIG. 1, a first memory may also be provided for storing the computer program to be executed in the processor, such as the gesture detection module described above. The ultrasound images herein may also be ultrasound images of different modes described above, such as B images, C images, D images, etc., or other types of two-dimensional ultrasound images or three-dimensional ultrasound images. Similarly, the ultrasound image mentioned herein may be a static frame image or a dynamic video image. In one embodiment, the ultrasound image may be a left ventricle long axis section image.

In step 440 of FIG. 4, the first processor 140 or the second processor 240 of FIG. 2 may output the obtained ultrasound image to the first display 130 or the second display for display. For example, an image display area for displaying the ultrasound image may be arranged on the graphical user interface layer formed on the display. In one embodiment, the graphical user interface may include at least two interface layers. The first interface layer of the touch screen may be used to display the ultrasound image, and the second interface layer that is transparent may be superimposed on the first interface layer. The editing information such as the marks, etc. may be arranged on the second interface layer. Such arrangement may allow other data than the image data to be displayed on the ultrasound image while not shade the ultrasound image itself, and enable the user to observe the change of the ultrasound image caused by the adjustment of the ultrasound imaging parameters or save and transfer the editing information along with the ultrasound image.

In step 450 of FIG. 4, the first processor 140 or the second processor 240 of FIG. 2 may acquire a mark point located in the active area of the mitral valve on the ultrasound image. This mark point may be located at any position within the active area of the mitral valve. The mitral valve mentioned herein may also be called as a sacral flap, which is like a "one-way valve" between the left atrium and the left ventricle and ensure that the blood circulation must be from the left atrium to the left ventricle and a certain blood flow will pass through. Therefore, the mitral valve active area contains an image area that constantly changes as the mitral valve pulsates with the heart.

In one embodiment, the mark point in the active area of the mitral valve may be a mark point input by the user through the human-machine interaction device, e.g., a mark point input when the user touches the area of the ultrasound image displayed on the touch screen. The mark point may be highlighted by various ways such as marking dots, marking circles, marking square lines, and the like. Therefore, the shape and expression form of the mark point are not limited. In one embodiment, the mark points in the step 450 above may be displayed on the second interface layer.

In another embodiment, the mark point in the active area of the mitral valve may be located at any position in the active area of the mitral valve that is automatically determined by the system, such as any position near the tip of the mitral valve, etc.

In one embodiment, the mark point in the active area of the mitral valve may be obtained by the user inputting an area range through the human-machine interaction device and then the system automatically determining any point in the region as the mark point. For example, when performing the above step 450, at least one of the following ways may be adopted:

1. obtaining a mark point input by the user on the ultrasound image through the human-machine interaction device; and, 2. obtaining an area range (for example, a mitral valve active region) defined by the user on the ultrasound image through the human-computer interaction device, and determining any position in the region as the position corresponding to the mark point.

In step 460 of FIG. 4, the first processor 140 or the second processor 240 of FIG. 2 may automatically search for a ventricular inner diameter reference point based on the mark point described above.

In one embodiment, the ventricular inner diameter reference point may deviate from a proximity point which is the point closest to the mitral valve tip position on the ventricular posterior wall skeleton line. Further, the ventricular inner diameter reference point may deviate from the proximity point in a direction away from the position of the mitral valve tip.

Based on the mark point manually input by the user on the ultrasound image or any position in the mitral valve active region automatically determined, the ventricular inner diameter reference point above may be quickly obtained in the following methods. In one embodiment, first, the first processor 140 may automatically search for the mitral valve tip position in the region where the mark point is located, and automatically search for the ventricular posterior wall skeleton line. For example, a connected area closest to the mark point may be automatically searched as the mitral valve active area and the mitral valve tip position may be extracted from the mitral valve active area, and a largest connected area (e.g., the area of the posterior wall of the ventricle) in the image may be searched and a center line of such area (e.g., the area of the posterior wall of the ventricle) in the length direction may be extracted, thereby obtaining the ventricular posterior wall skeleton line. Furthermore, in one embodiment, the left ventricular posterior wall area may be searched and the left ventricular posterior wall skeleton line may be extracted. Therefore, the ventricular posterior wall skeleton line in step 460 may be the left ventricular posterior wall skeleton line.

The first processor 140 may determine the ventricular inner diameter reference point according to the mitral valve tip position and the ventricular posterior wall skeleton line (e.g., the left ventricular posterior wall skeleton line). For example, the proximity point on the ventricular posterior wall skeleton line which is closest to the mitral valve tip may be found, and the ventricular inner diameter reference point may be obtained by moving the position of the proximity point with reference to the slope of the proximity point on the ventricular posterior wall skeleton line. In one embodiment, the point closest to the mitral valve on the left ventricular posterior wall skeleton line may be searched, and such point may be moved to the left with reference to the slope of such point on the left ventricular posterior wall skeleton line, thereby obtaining the ventricular inner diameter reference point.

In one embodiment, the process of automatically searching for the position of the mitral valve tip in the region where the mark point is located may be achieved in the following manner.

First, the connected area closest to the mark point may be automatically searched in the consecutive multiple frames of image to obtain the mitral valve active area of each frame of image.

Thereafter, the mitral valve tip position may be determined in the mitral valve active area of each frame of image, thereby obtaining the mitral valve tip position corresponding to each frame of image.

In the case that the distance between the mitral valve tip positions of two adjacent frames of image satisfying a predetermined condition is determined, the obtained mitral valve tip position may be retained; otherwise, in the case that the distance between the mitral valve tip positions of two adjacent frames of image not satisfying a predetermined condition is determined, the calculation result of the mitral valve tip position may be discarded. For example, the leftmost point of the mitral valve active area may be considered to be the mitral valve tip position. If the position of the mitral valve tip differs from the previous frame by more than 30, it is determined to be abnormal and should be discarded. The predetermined condition in this embodiment may be that the distance between the positions of the mitral valve tips obtained on two adjacent frames of images is less than a predetermined threshold.

In one embodiment, the process of automatically searching for the connected area closest to the mark point in the consecutive multiple frames of image to obtain the mitral valve active area corresponding to each frame of image may include the following steps: searching for the connected area closest to the mark point above in the first frame of image of the multiple frames of images as the mitral valve active area; in each of the other frames of images of the multiple frames of images, searching for a connected area closest to the connected area searched in the previous frame of image; outputting an alarm prompt to prompt that the output is invalid when it is determined that the connected areas respectively found in the consecutive multiple frames of images do not overlap (that is, each of the connected areas obtained in the consecutive multiple frames of images does not overlap with the connected area obtained in the previous frame of image) and not outputting the alarm prompt when the connected areas respectively found on the consecutive multiple frames of images overlap. The step of outputting the alarm prompt may remind the user to reprocess the output, thereby improving the calculation accuracy.

Further, in another embodiment, in the process of determining the distance between the mitral valve tip positions of two adjacent frames of image satisfying the predetermined condition and retaining the obtained mitral valve tip position, the judgment of the abnormality of the calculation result may also be performed. For example, when continuously obtained distances between the mitral valve tip positions of two adjacent frames of images do not satisfy the predetermined condition, an alarm prompt may be output to prompt that the output result is invalid.

In order to ensure that there is no false alarm or frequent alarm, the alarm prompt may be output only when it is continuously monitored that the connected areas respectively found on the consecutive multiple frames of images do not overlap. For example, in one embodiment, when the situation that the connected areas respectively found in the consecutive multiple frames of images do not overlap has occurred continuously for a time exceeding a time threshold, the alarm prompt may be output. The alarm prompt mentioned herein may employ a sound, a light, a vibration or any other way to prompt that the parameters output at this time are invalid. The time threshold may be 5 to 20 seconds.

In one embodiment, outputting the alarm prompt may be performed after the step of automatically searching for the ventricular posterior wall skeleton line. For example, the process of automatically searching for the ventricular posterior wall skeleton line may be implemented by searching for the left ventricular posterior wall area and extracting the skeleton line of the left ventricular posterior wall. The details are as follows.

For the pre-processed ultrasound image, the largest connected area may be found and determined as the left ventricular posterior wall area. Based on the determined left ventricular posterior wall area, the coordinates of the left ventricular posterior wall area may be averaged along the longitudinal direction, and the obtained points may be subjected to a quadratic curve fitting to obtain the left ventricular posterior wall skeleton line. For the coordinates of the left ventricular posterior wall area, the mean $\overline{L}(x)$ along the longitudinal direction may be calculated by the following formula.

$$\overline{L}(x) = \frac{1}{n} \sum_{y=y_{min}}^{y_{max}} L(x, y),$$

where L(x,y) is the coordinate of the left ventricular posterior wall area.

During this process, if the determined left ventricular posterior wall area is all above or to the right of the mitral valve tip, or there is no overlap with the left ventricular posterior wall area of the previous frame, it will be determined that the image quality is abnormal, and the left ventricular posterior wall area of the previous frame will be retained while the left ventricular posterior wall area of the current frame will be discarded. It can be seen that, in one embodiment, the first processor may automatically search for the maximum connected area and the connected area closest to the mark point in the ultrasound image, and output the alarm prompt to indicate that the output result is invalid when it is determined that the obtained maximum connected area and the obtained connected area closest to the mark point do not satisfy an anatomical structural characteristics, or the maximum connected areas obtained in two adjacent frames of ultrasound images do not overlap.

In order to ensure that there is no false alarm or frequent alarms, the alarm prompt may be output only when it is continuously monitored that the obtained maximum connected area and the obtained connected area closest to the mark point do not satisfy an anatomical structural characteristics or the maximum connected areas obtained in two adjacent frames of ultrasound images do not overlap. For example, in one embodiment, when the situation that the obtained maximum connected area and the obtained connected area closest to the mark point do not satisfy an anatomical structural characteristics or the maximum connected areas obtained in two adjacent frames of ultrasound images do not overlap has occurred continuously for a time exceeding a time threshold, the alarm prompt may be output. The alarm prompt mentioned herein may employ a sound, a light, a vibration or any other way to prompt that the parameters output at this time are invalid. The time threshold may be 5 to 20 seconds.

Figure 5A:
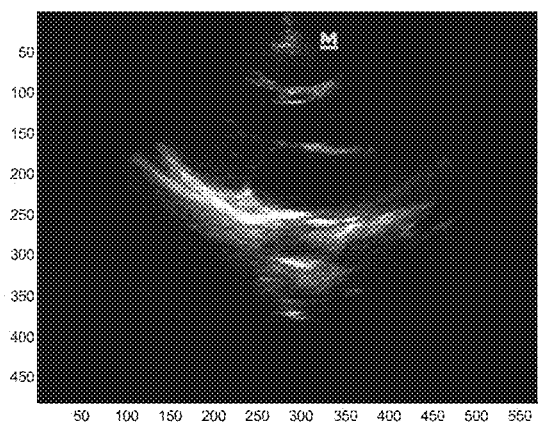
FIG. 5(A), FIG. 5(B), FIG. 5(C), FIG. 5(D), and FIG. 5(E) show the effects of the results of image processing obtained by performing the method shown in FIG. 4 taking a long-axis section image of the left ventricle as an example in one embodiment.

In order to improve the processing efficiency of automatically searching for the ventricular inner diameter reference point according to the mark point in the step 460 above, the step of automatically searching may be performed after performing a pre-processing on the obtained ultrasound image. The pre-processing on the ultrasound image may include the following processes:

First, consecutive multiple frames of ultrasound image in a predetermined time period (e.g., FIG. 5(A)) may be extracted. The predetermined time period may, for example, be 1 to 2 seconds.

Then, the variance of each point on the multiple frames of ultrasound images along the time axis may be calculated to obtain a variance image. For example, the variance s(x, y) may be obtained along the time axis for each point of the image in a time period T in the following manner:

$$s(x, y) = \left(\frac{1}{n}\sum_{j=1}^{n}(img(x, y, j) - \overline{img}(x, y))^2\right)^{\frac{1}{2}},$$

Where $$\overline{img}(x, y) = \frac{1}{n}\sum_{j=1}^{n}img(x, y, j),$$

x is the abscissa, y is the ordinate, j is the time axis coordinate, and n is the number of frames in the time period T.

Figure 5B:
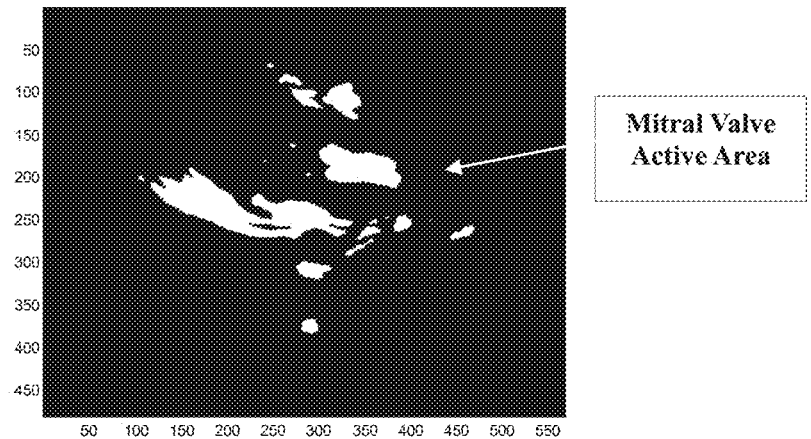

Next, the variance image above may be binarized to obtain a pre-processed ultrasound image (e.g., FIG. 5(B)) for performing the step 460 above. For example, a binarization process may be performed to obtain consecutive multiple frames of images. It can be seen that when the step S460 is performed based on the variance image, the accuracy and speed of the image processing may be improved, and the automatic image search may be accelerated. For example, FIG. 5(A) is an original image of the ultrasound image obtained by the image processor, and FIG. 5(B) is an ultrasound image after the variance calculation and binarization processing above. Both FIG. 5(A) and FIG. 5(B) are shown taking the left ventricular long axis section image as an example.

Figure 5C:
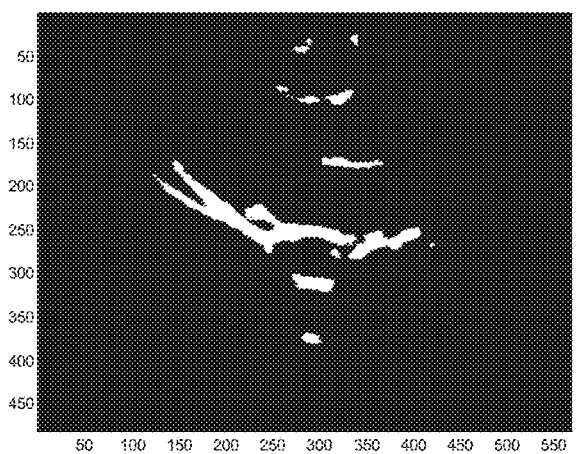
Figure 5D:
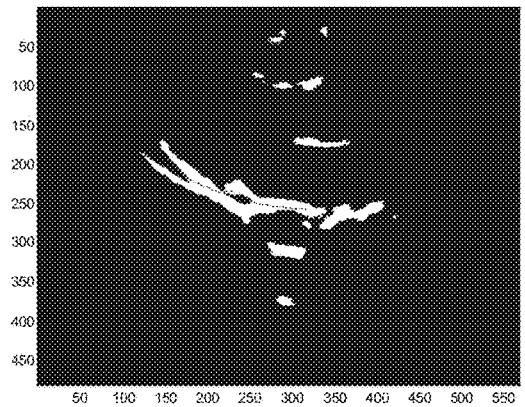

In order to reduce the amount of calculation, the binarization of the pre-processed ultrasound image may be performed before the process of searching for the ventricular posterior wall skeleton line in the step 460 to obtain the pre-processed image as shown in FIG. 5(C). Thereafter, the searching for the maximum connected area may be performed based on the pre-processed image to obtain the ventricular posterior wall area which may be used to extract the ventricular posterior wall skeleton line. Both FIG. 5(C) and FIG. 5(D) are shown taking the left ventricular long axis section image as an example. The maximum connected area shown in FIG. 5(C) is the left ventricular posterior wall area. The dotted line shown in FIG. 5(D) is the automatically extracted left ventricular posterior wall skeleton line. The position of the ventricular inner diameter reference point, such as the large white square, is provided in FIG. 5(E). The small white square in FIG. 5(E) indicates the position of the mitral valve tip, and the white line is the M line that passes the closest foot of perpendicular.

The pre-processing process of the image in the above process may further include pre-processing processes such as smoothing denoising of the ultrasound image, tissue contour enhancement, etc., so as to improve the image quality and clarify the tissue contour in the connected area in the image.

In step 470 of FIG. 4, the first processor 140 or the second processor 240 of FIG. 2 may calculate hemodynamic parameters based on the ventricular inner diameter reference point above. The hemodynamic parameters herein may include a number of indication parameters for evaluating the ventricular function, such as ventricular systolic ejection ability, i.e., ventricular pumping function, which is usually evaluated by cardiac output and ejection fraction, and ventricular diastolic function indicator used to represent the diastolic expansion ability of the ventricle, which is generally evaluated by indicators such as ventricular compliance. The cardiac output refers to the amount of blood output by the ventricle per minute, which is equal to the stroke volume multiplied by the heart rate. The ejection fraction is the percentage of the stroke volume to the ventricular end-diastolic volume. When the heart is active within the normal working range, the stroke volume is always compatible with the ventricular end-diastolic volume. Of course, the hemodynamic parameters may also include left ventricular volume indicators for clinical evaluation of left ventricular systolic function.

Figure 5E:
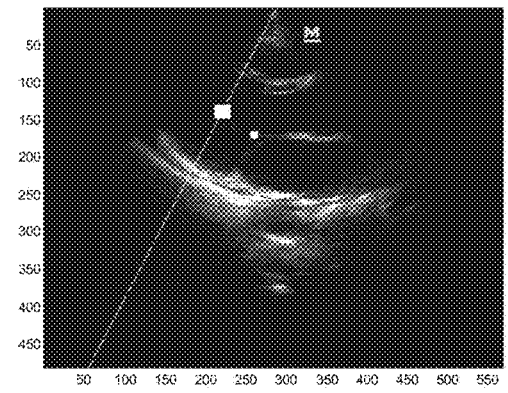
Figure 6A:
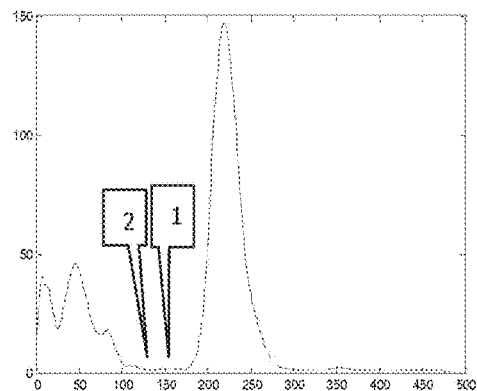
FIG. 6(A) shows the grayscale change of one M line in one embodiment.
Figure 6B:
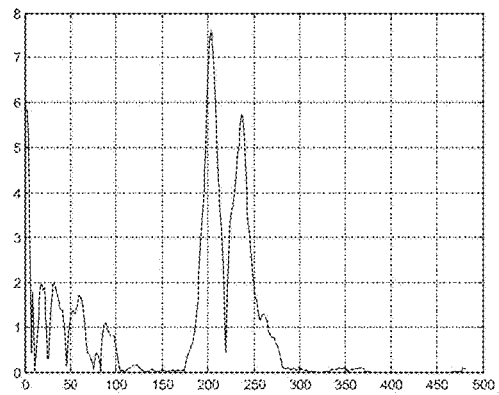
FIG. 6(B) shows the change of the gradient absolute value corresponding to FIG. 6(A), where

In one embodiment, the process of calculating the hemodynamic parameters according to the ventricular inner diameter reference point above may be achieved in the following manners in the step 470. First, an M line may be automatically obtained according to the ventricular inner diameter reference point, and thereafter, the hemodynamic parameters may be automatically calculated according to the M line. The white line as shown in FIG. 5(E) represents the M line, and an M image may be obtained based on the change of the grayscale of each point on the M line along the time axis. In FIG. 6(A) and FIG. 6(B), FIG. 6(A) is a grayscale diagram of one M line, where 1 corresponds to the ventricular inner diameter reference point, 2 corresponds to the valley point, and FIG. 6(B) shows corresponding absolute value of the gradient.

The process of automatically obtaining the M line according to the ventricular inner diameter reference point may adopt the manner in the following embodiments. The first processor may automatically search for the foot of perpendicular closest to the ventricular inner diameter reference point from the ventricular inner diameter reference point to the ventricular posterior wall skeleton line, and connect the ventricular inner diameter reference point with the nearest foot of perpendicular to obtain the M line. Specifically, the process may include segmenting the ventricular posterior wall skeleton line (e.g., the left ventricular posterior wall skeleton line) and making the foot of perpendicular from the ventricular inner diameter reference point for each segment, and finding the foot of perpendicular closest to the ventricular inner diameter reference point. After the steps of segmenting the ventricular posterior wall skeleton line, making the foot of perpendicular from the ventricular inner diameter reference point for each segment and finding the foot of perpendicular closest to the ventricular inner diameter reference point are completed, the coordinates of the foots of perpendicular on each frame within a time period T' may be averaged to achieve the effect of debounce. The time period T' may be 1 to 2 seconds.

In the process of automatically calculating the hemodynamic parameters according to the M line, first, the M line may be obtained according to the embodiments above, and thereafter, the M image may be plotted along the time axis according to the grayscale of each point on the M line. In one embodiment, the ventricular inner diameter may be obtained based on the M image. Specifically, it may be obtained in the following manner as shown in FIG. 6.

The upper and lower edges of the ventricle (e.g., the left ventricle) in the M image may be identified and extracted to obtain the distance between the upper and lower edges, which is the length of the inner diameter of the ventricle. Identifying and extracting the upper and lower edges of the ventricle in the M image may be implemented by the following manner. Taking the ventricular inner diameter reference point (e.g., 1 in FIG. 6(A)) as an initial point, the searching may be performed in the direction where the grayscale becomes lower (i.e., the grayscale is lower) until the first minimum point is obtained. Such first minimum point may be determined as the valley point, such as 2 in FIG. 6(A). Then, the searching may be performed from the valley point to each side until the first point where the gradient absolute value is greater than a predetermined threshold and behind which all points in a predetermined range have grayscales greater than that of such point is obtained. The searched points may be determined as the upper boundary point and the lower boundary point of the ventricular chamber. In the present embodiment, the predetermined threshold may be 1 to 2, and the predetermined range may be 20-40. In order to improve the smoothness of the boundary point extraction, the boundary points obtained by the search may be smoothed along the time axis to remove the glitch.

The process in the step 460 to step 470 above may be performed on the ultrasound images in the end-diastolic and/or end-systolic phase, i.e., automatically searching the ventricular inner diameter reference point according to the mark point, obtaining the M-line based on the ventricular inner diameter reference point, obtaining the M image based on the M-line, and obtaining the upper and lower boundary points of the ventricular chamber based on the M map, thereby obtaining the maximum and/or minimum of the ventricular inner diameter length, that is, obtaining the end-diastolic ventricular inner diameter and/or the end-systolic ventricle inner diameter to calculate the hemodynamic parameters. According to the obtained end-diastolic ventricular inner diameter and end-systolic ventricular inner diameter, the end-diastolic left ventricular volume and the end-systolic left ventricular volume may be calculated according to Cube or Teichholz or Gibson formula, and other corresponding clinical indicators may also be calculated. For example, the other clinical indicators corresponding to the end-diastolic left ventricular volume and the end-systolic left ventricular volume may include the hemodynamic parameters such as ejection fraction, stroke volume, and stroke index, etc. In one embodiment, in the step 470, the left ventricular section ultrasound image may be used to calculate the hemodynamic parameters, such as the left ventricular long-axis section image, thereby obtaining the hemodynamic parameters such as left ventricular end-systolic short-axis inner diameter (EDS), left ventricular end-diastolic short-axis inner diameter (EDD), left anterior ejection time (ET), heart rate (HR), left ventricular end-systolic volume (ESV), left ventricular end-diastolic volume (EDV), stroke volume (SV), cardiac output (CO), left ventricular ejection fraction (EF), left ventricular short axis shortening fraction (FS), mean left ventricular peripheral shortening velocity (Vcf), mean left ventricular systolic ejection rate (MSER), etc.

In step 480 of FIG. 4, the first processor 140 or the second processor 240 of FIG. 2 may output the calculation result of the hemodynamic parameters. The calculation result of the output hemodynamic parameters may be displayed on the display interface of the display through text, voice prompt, etc., or be output through a printer, a fax machine, or the like. Alternatively, the calculated hemodynamic parameters may be transmitted to the ultrasound display terminal of FIG. 2 such as the workstation, server, mobile terminal, etc., through network transmission for storage or display.

Figure 7:
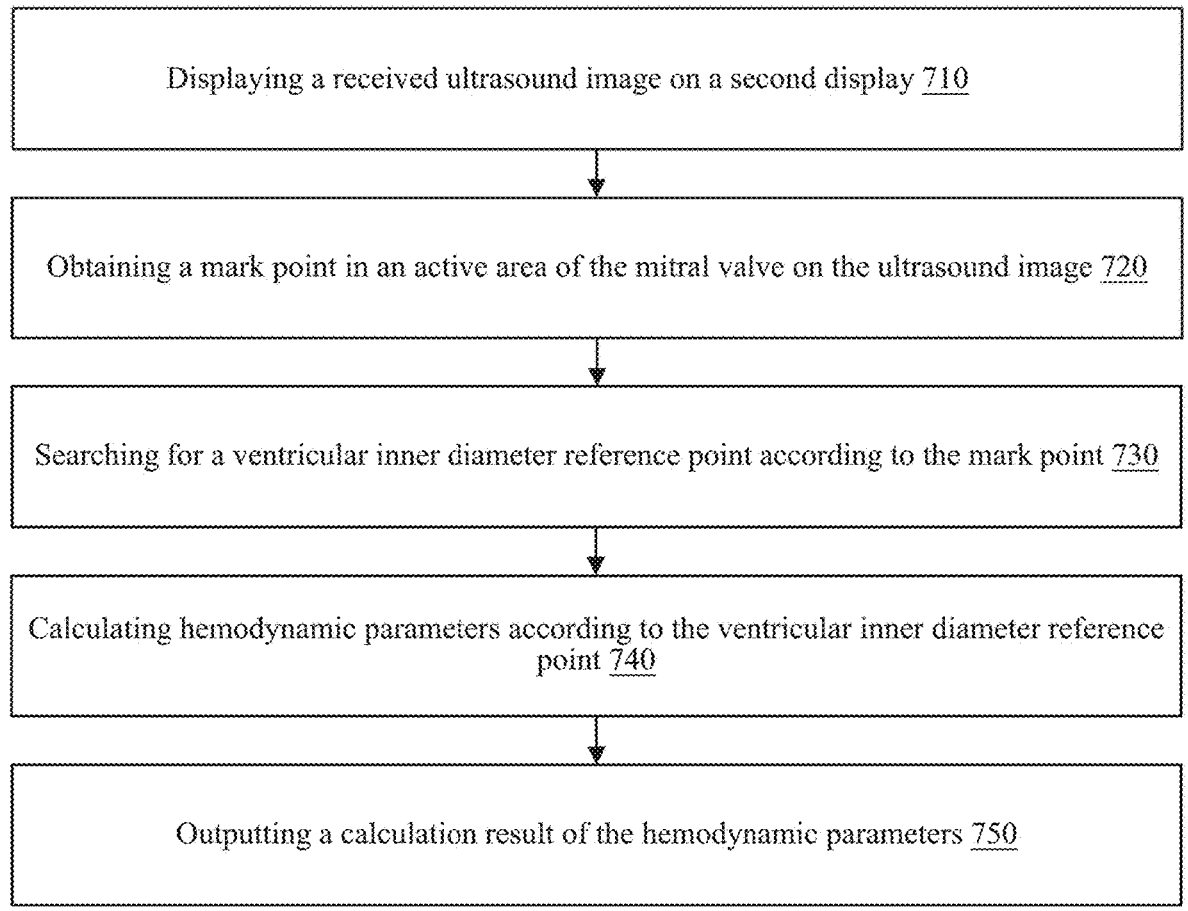
FIG. 7 is a flowchart of an example method in the embodiment shown in FIG. 2.

Furthermore, based on the system architecture shown in FIG. 2, the mark point located in the active area of the mitral valve in the ultrasound image may be obtained by the ultrasound display terminal 270, thereby calculating the hemodynamic parameters based on the mark point. For example, in one embodiment, an ultrasound imaging system is provided that may include an ultrasound medical detection device 200 and an ultrasound display terminal 270. The ultrasound medical detection device 200 may include a probe 201, a transmitting circuit 203, a receiving circuit 204, an image processor 226, and a first communication device 215 connected with the image processor. The transmitting circuit 203 and the receiving circuit 204 may be configured to excite the probe to transmit an ultrasound beam to an object containing heart tissue and receive echoes of the ultrasound beam to obtain an ultrasound echo signal. The image processor 226 may be configured to obtain an ultrasound image based on the ultrasound echo signals, such as an M-mode echocardiogram. The first communication device 215 may be configured to transmit the ultrasound image to the ultrasound display terminal 270. The ultrasound display terminal 270 may include a second display, a second communication device 214, a second memory 260 and a second processor 240. The second communication device 214 may receive the ultrasound image transmitted from the first communication device, and the second memory 260 may store the computer programs to be executed by the processor. The system architecture of FIG. 2 will not be described in detail here and reference may be made to the related description above. FIG. 7 illustrates a flowchart of example steps the second processor 240 may implement when executing the program stored in the second memory 260:

step 710: displaying the received ultrasound image on the second display, step 720: obtaining a mark point in the active area of the mitral valve on the ultrasound image, step 730: automatically searching for the ventricular inner diameter reference point according to the mark point, step 740: calculating the hemodynamic parameters according to the ventricular inner diameter reference point, and, step 750: outputting the calculation result of the hemodynamic parameters.

In addition, based on the ultrasound imaging system above, as a separate execution body, such as the ultrasound display terminal 270, there may be also provided an ultrasound display terminal 270 which may include a second display, a second communication device 214, a second memory 260 and a second processor 240. The second processor 240 may implement the step 710 to step 750 when executing the program stored in the second memory 260.

As shown in FIG. 7, regarding the execution process of the steps 710 to 750, reference may be made to the execution process of the foregoing steps 440 to 480 in FIG. 4. Except that the execution object is different, the details of the execution may be the same as those described above, and will not be described again here. Of course, for complex image processing operations, it may not be executed by a CPU built in a mobile terminal device such as a mobile phone or an IPad, etc., but may be executed by a cloud computing server, a remote server, or the like. Alternatively, the image processing operations may also be implemented by frequent data transmission with the image processor in the ultrasound medical detection device 200. These variations may all be equivalent to being performed by the second processor of the ultrasound display terminal 270.

In one embodiment, in the step 710, the ultrasound image obtained by the second processor 240 in FIG. 2 may be transmitted by the ultrasound medical detection device 200 to the ultrasound display terminal 270 through the first communication device, and be displayed on the ultrasound display terminal 270. The ultrasound image may be used for obtaining the mark point in the step 450 based on the human-machine interaction device in the ultrasound display terminal 270. For example, the mark point may be input by touching a certain point in the ultrasound image display area on the touch screen of the ultrasound display terminal 270. Alternatively, the area range mentioned above may be input by touching a certain area range containing the mitral valve active area in the ultrasound image display area on the touch screen of the ultrasound display terminal 270, and any one position in the area range may be determined as the position of the mark point above.

What FIG. 4 provides is only one execution sequence of the steps. Various modifications may be obtained by adjusting the sequence of the steps in FIG. 4. The steps are not limited to being performed only in the order of FIG. 4. Satisfying the basic logic, the steps may be replaced with each other, or the execution sequence may be changed, or last one or more of the steps may be performed after one or more of the steps are repeatedly executed. These solutions are all variants obtained according to the embodiments provided herein. Of course, the different steps can be completed by different execution bodies, as described above.

Through the description of the embodiments above, those skilled in the art can clearly understand that the methods in the foregoing embodiment can be implemented by means of software plus a necessary general hardware platform. Alternatively, they can also be implemented by hardware. Based on this understanding, the essential part or the part contributing to the prior art of the technical solution of the present disclosure may be embodied in the form of a software product. The software product may be carried on a non-transitory computer readable storage medium (e.g., ROM, disk, optical disk, hard disk, server cloud space), and may include a plurality of instructions which may enable a terminal device (which may be a mobile phone, a computer, a server, a network device, etc.) to execute the system structures and methods of the embodiments of the present disclosure. For example, a computer readable storage medium may store thereon a computer program. The computer program may, when executed by a processor, be used to at least implement various embodiments based on the flowchart shown in step 440 to step 480 of FIG. 4.

In the embodiments above, a semi-automatic or fully automatic method for calculating the hemodynamic parameters such as ventricular volume is provided, which can, after the user manually marks one feature point (such as the mark point above) or an area range, continuously automatically calculate the ventricular volume and the corresponding hemodynamic parameters such as ejection fraction (EF), stroke volume (SV) and stroke index (SI), etc. in real time. In one embodiment, the hemodynamic parameters of the left ventricle, such as the left ventricular volume, etc., can be particularly calculated. In the embodiments above, a fully automatic method for calculating the hemodynamic parameters such as ventricular volume, etc. may also be provided, in which the hemodynamic parameters can be automatically calculated according to the foregoing methods after the system extracts the mark point above. The methods of the present embodiment are adaptive. When the position of the heart changes, the algorithm can adaptively adjust the measurement position by tracking the positions of key areas, such as the mitral valve and the left ventricular posterior wall, etc. When the image quality does not meet the requirements, e.g., when the critical area is not visible, the algorithm will raise an alarm. Again, the methods support long-term monitoring of the heart. The embodiments can achieve non-invasive, adaptive, low-cost cardiac parameter monitoring for the human body.

The embodiments above merely show several embodiments, the description of which is relatively specific and detailed. However, it shall not be construed as limitation to the scope of the present disclosure. It should be noted that a number of variations and modifications may be made by those skilled in the art without departing from the conception of the present disclosure, which shall all be in the scope of the present disclosure. Therefore, the scope of the present disclosure should be determined by the appended claims.

The invention claimed is:

1. An ultrasound medical detection device, comprising:
a probe;

a transmitting circuit configured to excite the probe to transmit an ultrasound beam to an object containing a heart tissue;

a receiving circuit configured to obtain an ultrasound echo signal from an echo of the ultrasound beam;

a display;

a processor;

a memory storing instructions that, when executed by the processor, cause the device to perform:

obtaining an ultrasound image according to the ultrasound echo signal;

displaying the ultrasound image on the display;

obtaining a mark point located in a mitral valve active area on the ultrasound image;

determining a ventricular inner diameter reference point according to the mark point;

calculating a hemodynamic parameter according to the ventricular inner diameter reference point; and outputting the calculated hemodynamic parameter.

2. The ultrasound medical detection device of claim 1, wherein the ultrasound image is a left ventricular long axis section image.

3. The ultrasound medical detection device of claim 1, wherein the calculating the hemodynamic parameter according to the ventricular inner diameter reference point, comprises:

obtaining a M line according to the ventricular inner diameter reference point; and calculating the hemodynamic parameter according to the M line.

4. The ultrasound medical detection device of claim 3, wherein the obtaining the M line according to the ventricular inner diameter reference point, comprises:

determining a foot of perpendicular of the ventricular posterior wall skeleton line closest to the ventricular inner diameter reference point;

obtaining the M line by connecting the ventricular inner diameter reference point and the foot of perpendicular.

5. The ultrasound medical detection device of claim 3, wherein the calculating the hemodynamic parameter according to the M line, comprises:

drawing an M image along a time axis according to grayscale of each point on the M line;

extracting an upper edge and a lower edge of a ventricle in the M image to obtain a ventricular inner diameter length; and obtaining a maximum or a minimum of the ventricular inner diameter length based on the ultrasound images in an end-diastolic or an end-systolic phase to calculate the hemodynamic parameter.

6. The ultrasound medical detection device of claim 1, wherein the determining the ventricular inner diameter reference point according to the mark point, comprises:

determining a position of a mitral valve tip in an area of the mark point;

determining a ventricular posterior wall skeleton line;

determining a proximity point on the ventricular posterior wall skeleton line closest to the mitral valve tip; and obtaining the ventricular inner diameter reference point by moving a position of the proximity point based on a slope of the proximity point.

7. The ultrasound medical detection device of claim 6, wherein the determining the position of the mitral valve tip in the area of the mark point further comprises:

determining a connected area closest to the mark point obtaining the position of the mitral valve tip by a determined connected area;

wherein the determining the ventricular posterior wall skeleton line further comprises:

determining a largest connected area; and extracting a center line of the larges connected area along a length direction thereof.

8. The ultrasound medical detection device of claim 1, wherein, the ventricular inner diameter reference point deviates from a proximity point, wherein the proximity point is a position on a ventricular posterior wall skeleton line which is closest to a position of a mitral valve tip, and wherein the ventricular inner diameter reference point deviates from the proximity point in a direction away from the position of the mitral valve tip.

9. The ultrasound medical detection device of claim 1, wherein the obtaining the mark point located in the mitral valve active area on the ultrasound image, comprises:

obtaining the mark point on the ultrasound image through a human-machine interaction device;

obtaining an area range containing the mitral valve active area through the human-machine interaction device; and determining positions of any point in the area range as a position corresponding to the mark point.

10. The ultrasound medical detection device of claim 1, wherein the instructions, executed by the processor, cause the device to perform:

outputting an alarm prompt to prompt that an output result is invalid.

11. The ultrasound medical detection device of claim 10, further comprising:

determining connected areas closest to the mark point in consecutive multiples images, and outputting the alarm prompt when the connected areas obtained in the consecutive multiple images do not overlap; or determining a maximum connected area and a connected area closest to the mark point in the ultrasound image, and outputting the alarm prompt when the maximum connected area and the obtained connected area closest to the mark point do not satisfy an anatomical structure characteristic or the maximum connected areas obtained in adjacent two frames of ultrasound images do not overlap.

12. An ultrasound imaging method comprising:

displaying an ultrasound image on a display, wherein the ultrasound image is obtained according to an ultrasound echo signal, and wherein the ultrasound echo signal is obtained by receiving an echo of an ultrasound beam wherein the ultrasound beam is transmitted to an object containing a heart tissue by exciting a probe;

obtaining a mark point in a mitral valve active area in the ultrasound image;

determining a ventricular inner diameter reference point according to the mark point; and calculating a hemodynamic parameter according to the inner diameter reference point.

13. The ultrasound imaging method of claim 12, wherein the ultrasound image is a left ventricular long axis section image.

14. The ultrasound imaging method of claim 12, wherein calculating the hemodynamic parameter according to the inner diameter reference point comprises:

obtaining an M line according to the ventricular inner diameter reference point; and calculating the hemodynamic parameter according to the M line.

15. The ultrasound imaging method of claim 14, wherein automatically obtaining the M line according to the ventricular inner diameter reference point comprises:
 searching for a foot of perpendicular from the ventricular inner diameter reference point to the ventricular posterior wall skeleton line which is closest to the ventricular inner diameter reference point; and
 connecting the ventricular inner diameter reference point and the foot of perpendicular to obtain the M line.

16. The ultrasound imaging method of claim 14, wherein calculating the hemodynamic parameter according to the M line comprises:
 drawing an M image along a time axis according to grayscale of each point on the M line;
 extracting an upper edge and a lower edge of a ventricle in the M image to obtain a ventricular inner diameter length; and
 obtaining a maximum or a minimum of the ventricular inner diameter length based on the ultrasound images in an end-diastolic or an end-systolic phase to calculate the hemodynamic parameter.

17. The ultrasound imaging method of claim 12, wherein determining the ventricular inner diameter reference point according to the mark point comprises:
 determining a position of a mitral valve tip in an area where the mark point is located;
 determining a ventricular posterior wall skeleton line;
 determining a proximity point on the ventricular posterior wall skeleton line closest to the position of the mitral valve tip; and
 obtaining the ventricular inner diameter reference point by moving a position of the proximity point based on a slope of the proximity point.

18. The ultrasound imaging method of claim 17, wherein determining the position of the mitral valve tip in the area where the mark point is located comprises: determining a connected area closest to the mark point to obtain the position of the mitral valve tip; and
 wherein determining the ventricular posterior wall skeleton line comprises: determining a largest connected area and extracting a center line of the largest connected area along a length direction thereof to obtain the ventricular posterior wall skeleton line.

19. The ultrasound imaging method of claim 12, wherein, the ventricular inner diameter reference point deviates from a proximity point, wherein the proximity point is a position on a ventricular posterior wall skeleton line closest to a position of a mitral valve tip, and
 wherein the ventricular inner diameter reference point deviates from the proximity point in a direction away from the position of the mitral valve tip.

20. The ultrasound imaging method of claim 12, wherein obtaining the mark point in the mitral valve active area in the ultrasound image comprises:
 obtaining the mark point on the ultrasound image through a human-machine interaction device; or
 obtaining an area range containing the mitral valve active area on the ultrasound image through a human-machine interaction device; and
 determining a position of any point in the area range as a position corresponding to the mark point.

21. The ultrasound imaging method of claim 12, further comprising:
 outputting an alarm prompt to prompt that an output result is invalid.

22. The ultrasound imaging method of claim 21, wherein outputting the alarm prompt to prompt that the output result is invalid comprises:
 determining connected areas closest to the mark point in consecutive multiples images,
 outputting the alarm prompt when it is determined that the connected areas respectively obtained in the consecutive multiple images do not overlap;
or
 determining a maximum connected area and a connected area closest to the mark point in the ultrasound image;
 outputting the alarm prompt when the maximum connected area and the obtained connected area closest to the one marked point do not satisfy an anatomical structure characteristic or the maximum connected areas obtained in adjacent two ultrasound images do not overlap.

23. An ultrasound imaging system, comprising
an ultrasound medical detection device; and
an ultrasound display terminal;
wherein the ultrasound medical detection device comprises:
a probe;
a transmitting circuit configured to excite the probe to transmit an ultrasound beam to an object containing a heart tissue;
a receiving circuit configured to obtain an ultrasound echo signal from an echo of the ultrasound beam;
an image processor configured to obtain an ultrasound image according to the ultrasound echo signal; and
a first communication device connected with the image processor, configured to transmit the ultrasound image to the ultrasound display terminal; and
wherein the ultrasound display terminal comprises:
a display,
a second communication device configured to receive the ultrasound image transmitted from the first communication device;
a memory storing instructions that, when executed by a processor, cause the system to perform:
displaying the ultrasound image on the display;
obtaining a mark point located in a mitral valve active area on the ultrasound image;
determining a ventricular inner diameter reference point according to the mark point;
calculating a hemodynamic parameter according to the ventricular inner diameter reference point; and
outputting a calculation result of the hemodynamic parameter.

24. An ultrasound display terminal, comprising:
a display;
a communication device configured to receive an ultrasound image transmitted from an ultrasound medical detection device;
a memory storing instructions that, executed by a processor, cause the system to perform:
displaying the ultrasound image on the display;
obtaining a mark point located in a mitral valve active area on the ultrasound image;
determining a ventricular inner diameter reference point according to the mark point;
calculating a hemodynamic parameter according to the ventricular inner diameter reference point; and
outputting a calculation result of the hemodynamic parameter.

25. A non-transitory computer readable storage medium having stored thereon instructions which, when executed by a processor, cause the processor to: display an ultrasound image on a display; obtain a mark point in a mitral valve active area in the ultrasound image; determine a ventricular inner diameter reference point according to the mark point; and calculate a hemodynamic parameter according to the inner diameter reference point.

\* \* \* \* \*